(12) United States Patent
Ichihashi et al.

(10) Patent No.: US 8,721,524 B2
(45) Date of Patent: May 13, 2014

(54) ENDOSCOPE WITH THIN PLATE-LIKE SUBSTRATE

(75) Inventors: Masaki Ichihashi, Kokubunji (JP); Yasundo Tanaka, Hino (JP)

(73) Assignee: Olympus Corporation (JP)

( * ) Notice: Subject to any disclaimer, the term of this patent is extended or adjusted under 35 U.S.C. 154(b) by 1272 days.

(21) Appl. No.: 12/146,929

(22) Filed: Jun. 26, 2008

(65) Prior Publication Data
US 2009/0012358 A1    Jan. 8, 2009

(30) Foreign Application Priority Data

Jul. 2, 2007    (JP) ................................. 2007-174565

(51) Int. Cl.
*A61B 1/00*    (2006.01)
*A61B 1/04*    (2006.01)
*A61B 1/06*    (2006.01)

(52) U.S. Cl.
USPC ........... 600/110; 600/109; 600/160; 600/172; 600/175

(58) Field of Classification Search
USPC .......................... 600/109, 160, 172, 175, 110
See application file for complete search history.

(56) References Cited

U.S. PATENT DOCUMENTS

| | | | | |
|---|---|---|---|---|
| 4,741,327 A * | 5/1988 | Yabe | ............................. | 600/130 |
| 5,140,265 A * | 8/1992 | Sakiyama et al. | ............ | 324/220 |
| 5,634,466 A * | 6/1997 | Gruner | .......................... | 600/459 |
| 6,796,939 B1 * | 9/2004 | Hirata et al. | ................... | 600/179 |
| 2002/0161284 A1 * | 10/2002 | Tanaka | ........................... | 600/176 |
| 2003/0060679 A1 * | 3/2003 | Murata et al. | ................. | 600/111 |
| 2003/0236443 A1 * | 12/2003 | Cespedes et al. | ............... | 600/29 |
| 2005/0182291 A1 * | 8/2005 | Hirata | ............................ | 600/101 |
| 2006/0025691 A1 * | 2/2006 | Tanaka et al. | .................. | 600/459 |
| 2006/0183977 A1 * | 8/2006 | Ishigami et al. | .............. | 600/179 |
| 2007/0106119 A1 * | 5/2007 | Hirata et al. | ................... | 600/179 |
| 2007/0249907 A1 * | 10/2007 | Boulais et al. | ................ | 600/179 |
| 2008/0091064 A1 * | 4/2008 | Laser | ............................ | 600/109 |

FOREIGN PATENT DOCUMENTS

| | | |
|---|---|---|
| JP | 2002-058636 | 2/2002 |
| JP | 2004-248835 | 9/2004 |
| JP | 2005-027851 | 2/2005 |
| JP | 2005-177134 | 7/2005 |
| JP | 2007-007092 | 1/2007 |
| JP | 2007-007338 | 1/2007 |

OTHER PUBLICATIONS

Office Action issued by the Japanese Patent Office on Apr. 24, 2012 in connection with corresponding Japanese Patent Application No. 2007-174565.

Japanese Office Action mailed Dec. 25, 2012 in connection with corresponding Japanese Application No. 2007-174565.

* cited by examiner

*Primary Examiner* — John P Leubecker
*Assistant Examiner* — Arnaldo Torres Diaz
(74) *Attorney, Agent, or Firm* — Ostrolenk Faber LLP (57) ABSTRACT

An endoscope according to the present invention includes: an elongated insertion portion inserted in an examination object; an LED which is provided in a distal end portion of the insertion portion and is driven by supply of electric power; an image pickup portion which is provided in the distal end portion on a rear end side in the insertion direction than the LED, and which picks up an image of the examination object; a power supply line for power supply, a distal end in an insertion direction of which is positioned in the distal end portion on a rear end side in the insertion direction than the image pickup portion, and which is inserted in the insertion portion.

29 Claims, 8 Drawing Sheets

ENDOSCOPE WITH THIN PLATE-LIKE SUBSTRATE

CROSS REFERENCE TO RELATED APPLICATION

This application claims benefit of Japanese Patent Application No. 2007-174565 filed in Japan on Jul. 2, 2007, the contents of which are incorporated by this reference.

BACKGROUND OF THE INVENTION

1. Field of the Invention

The present invention relates to an endoscope in which electrical components are provided in a distal end portion on a distal end side in an insertion direction of an elongated insertion portion inserted into an examination object, or provided in an adapter which is detachably attached to the distal end portion.

2. Description of the Related Art

As is well known, endoscopes have been widely used in medical fields and industrial fields. An endoscope used in a medical field is capable of observing an organ in a body cavity as an examination subject by inserting an elongated insertion portion into the body cavity, and further performing various treatment by using a treatment tool inserted into an insertion channel of the treatment tool, as required.

Further, an endoscope used in an industrial field is capable of performing observation of damage, corrosion, and the like, in examination objects, or performing various treatment, and the like, by inserting an elongated insertion portion into the inside of a jet engine, a pipe in a plant, and the like, which are the examination objects. Therefore, the industrial endoscope is generally used in an outdoor working facility, a working facility in a plant, and the like.

In the distal end portion on the distal end (hereinafter referred to simply as distal end) side in the insertion direction of the insertion portion of the endoscope, there are provided an image pickup portion including an objective optical system and an image pickup device such as a CCD, electrical components including a light source, such as an LED for illuminating an examination object, and a temperature sensor for measuring the temperature in the distal end portion, and the like.

Note that there is also known a configuration in which the objective optical system and the electrical components are provided in an adapter detachably attached to the distal end portion of the insertion portion. In this case, the temperature sensor configuring the electrical component measures the temperature in the adapter.

Meanwhile, as a configuration for supplying electric power to the electrical components provided in the distal end portion or in the adapter, there has been generally adopted a configuration in which the electric power from a power supply is supplied to the electrical components by using a power supply medium, for example, a power supply line for power supply, which is electrically connected to the electrical components and is inserted in the insertion portion of the endoscope.

For example, there is disclosed, in Japanese Patent Application Laid-Open Publication No. 2007-007338, a configuration in which there are provided, in the distal end portion of the insertion portion, a light source, and an electrical cable electrically connected to a connection pin of the light source and extended from a power supply for supplying electric power to the light source.

SUMMARY OF THE INVENTION

Simply, an endoscope according to the present invention includes: an elongated insertion portion inserted in an examination object; an electrical component which is provided in a distal end portion on a distal end side in an insertion direction of the insertion portion and is driven by supply of electric power; an image pickup portion which is provided in the distal end portion on a rear end side in the insertion direction than the electrical component, and which picks up an image of the examination object; a power supply line for power supply, a distal end in the insertion direction of which is positioned in the distal end portion on the rear end side in the insertion direction than the image pickup portion, and which is inserted in the insertion portion; and a thin plate-like flexible substrate which is inserted in a position between an outer circumference of the image pickup portion in the distal end portion and an inner circumference of the distal end portion, and which electrically connects a contact of the electrical component to the distal end of the power supply line.

Further, an endoscope according to the present invention includes: an elongated insertion portion inserted in an examination object; an electrical component which is provided in an adapter attached to a distal end portion on a distal end side in an insertion direction of the insertion portion, and is driven by supply of electric power; an image pickup portion which is provided in the distal end portion, and which picks up an image of the examination object; a power supply line for power supply, a distal end in the insertion direction of which is positioned on a rear end side in the insertion direction than the image pickup portion, and which is inserted in the insertion portion; and a thin plate-like flexible substrate which is inserted in a position between an outer circumference of the image pickup portion in the distal end portion and an inner circumference of the distal end portion, and which electrically connects a contact of the electrical component in the adapter to the distal end of the power supply line.

Further, an endoscope according to the present invention includes: an elongated insertion portion inserted in an examination object; an electrical component which is provided in an adapter detachably attached to a distal end portion on a distal end side in the insertion direction of the insertion portion, and is driven by supply of electric power; an image pickup portion which is provided in the distal end portion and picks up an image of the examination object; a power supply line for power supply, a distal end in the insertion direction of which is positioned on a rear end side in the insertion direction than the image pickup portion, and which is inserted in the insertion portion; a first thin plate-like flexible substrate which is inserted in a position between an outer circumference of the image pickup portion in the distal end portion and an inner circumference of the distal end portion, and which electrically connects a first contact of the electrical component in the distal end portion to the distal end of the power supply line; and a second thin plate-like flexible substrate which, when the adapter is attached to the distal end portion, electrically connects, in the adapter, a second contact of the electrical component connected to the first contact, to a third contact of the electrical component.

The above and other objects, features and advantages of the invention will become more clearly understood from the following description referring to the accompanying drawings.

DETAILED DESCRIPTION OF THE PREFERRED EMBODIMENTS

In the following, embodiments according to the present invention will be described with reference to the accompanying drawings. Note that an endoscope according to the present embodiment will be described by taking as an example a shoulder type industrial endoscope which is excellent in portability.

First Embodiment

Figure 1:
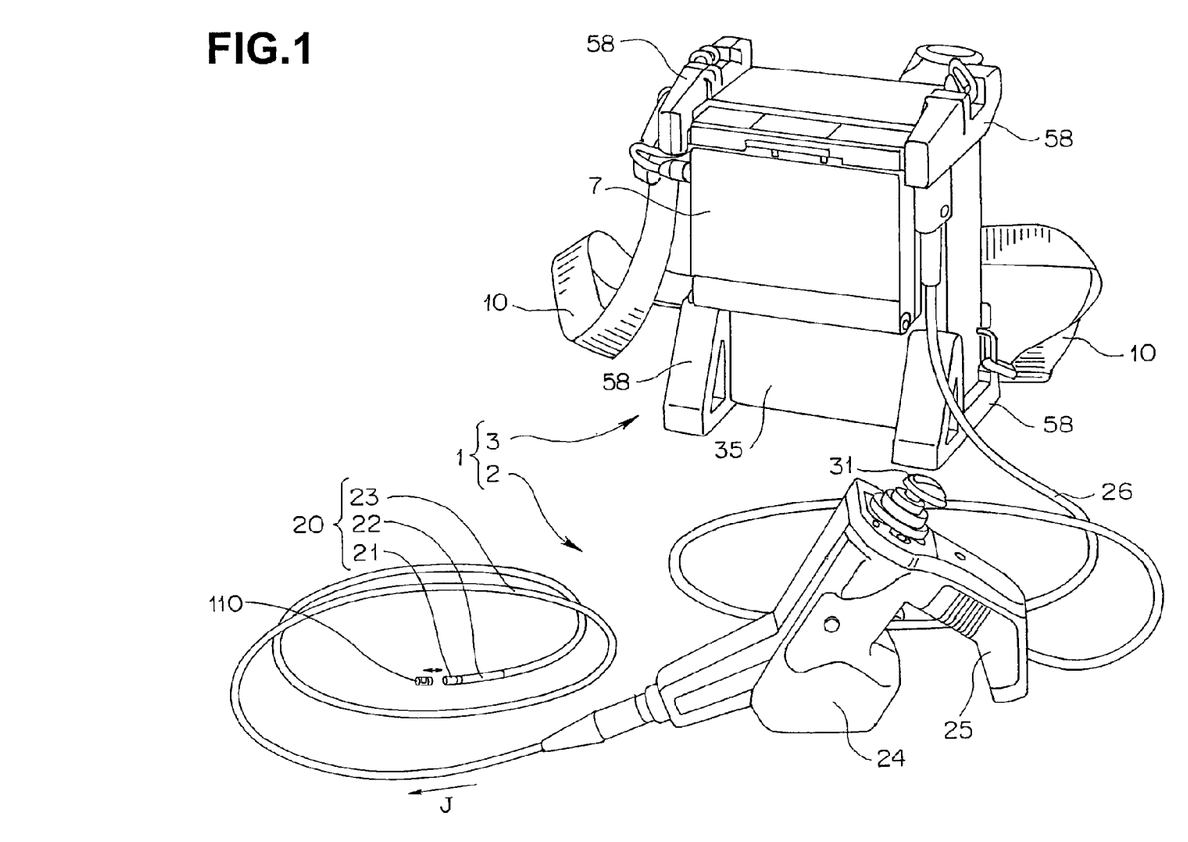
FIG. 1 is a perspective view showing an endoscope apparatus including an endoscope according to a first embodiment of the present invention.
Figure 2:
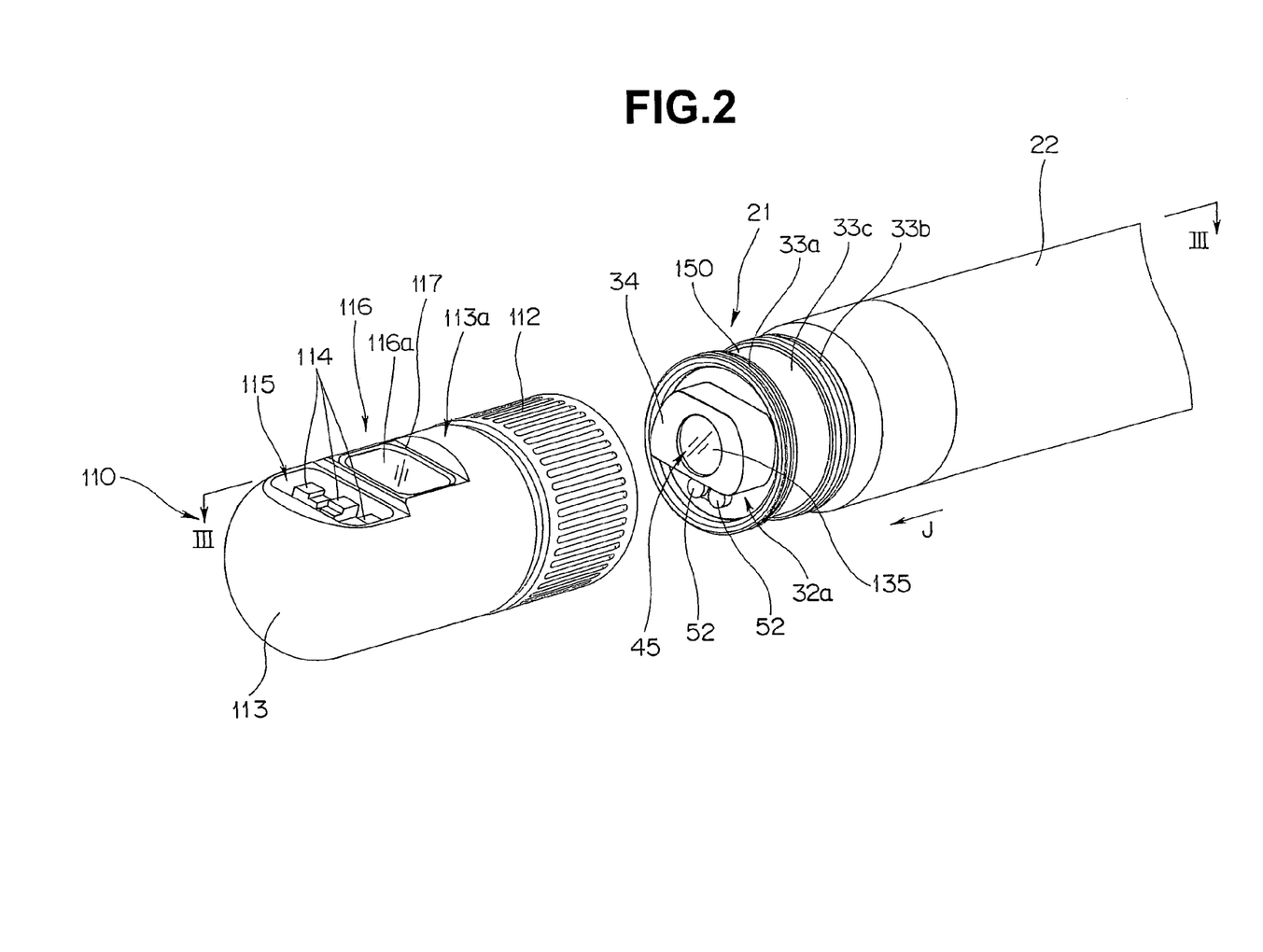
FIG. 2 is a partial perspective view showing an adapter which is detachably attached to the distal end side of an insertion portion and to a distal end portion of the insertion portion of the endoscope shown in FIG. 1.

FIG. 1 is a perspective view showing an endoscope apparatus including an endoscope according to the present embodiment. FIG. 2 is a partial perspective view showing an adapter which is detachably attached to the distal end side of an insertion portion and to a distal end portion of the insertion portion of the endoscope shown in FIG. 1.

As shown in FIG. 1, a main part of an endoscope apparatus 1 is configured by an endoscope 2, and an apparatus main body 3 to which the endoscope 2 is connected and which is an external device.

A main part of the endoscope 2 is configured by an elongated flexible insertion portion 20 having a small diameter of, for example, 4 mm, an operation portion 24 which is connected to the rear end in the insertion direction J (hereinafter referred to simply as rear end) of the insertion portion 20 and has a grasping portion 25, and a flexible universal cord 26 extended from the grasping portion 25 of the operation portion 24.

In the insertion portion 20, there are provided successively from the distal end side in the insertion direction J (hereinafter referred to simply as distal end side) of the insertion portion 20, a distal end portion 21, a bending portion 22 which is bent, for example, in the up and down left and right directions by a bending operation of a bending operation lever 31 of the operation portion 24, and a long flexible tube portion 23 formed of a flexible member. A rear end portion of the flexible tube portion 23 is connected to the operation portion 24.

In the operation portion 24, the bending operation lever 31 for performing the bending operation of the bending portion 22 is provided upright so as to be freely inclined in at least four directions.

By changing the inclined direction of the bending operation lever 31, an operator performs the bending operation of the bending portion 22 in one of four (up and down/right and left) directions via a bending operation wire 131 (see FIG. 3) as will be described below.

Figure 3:
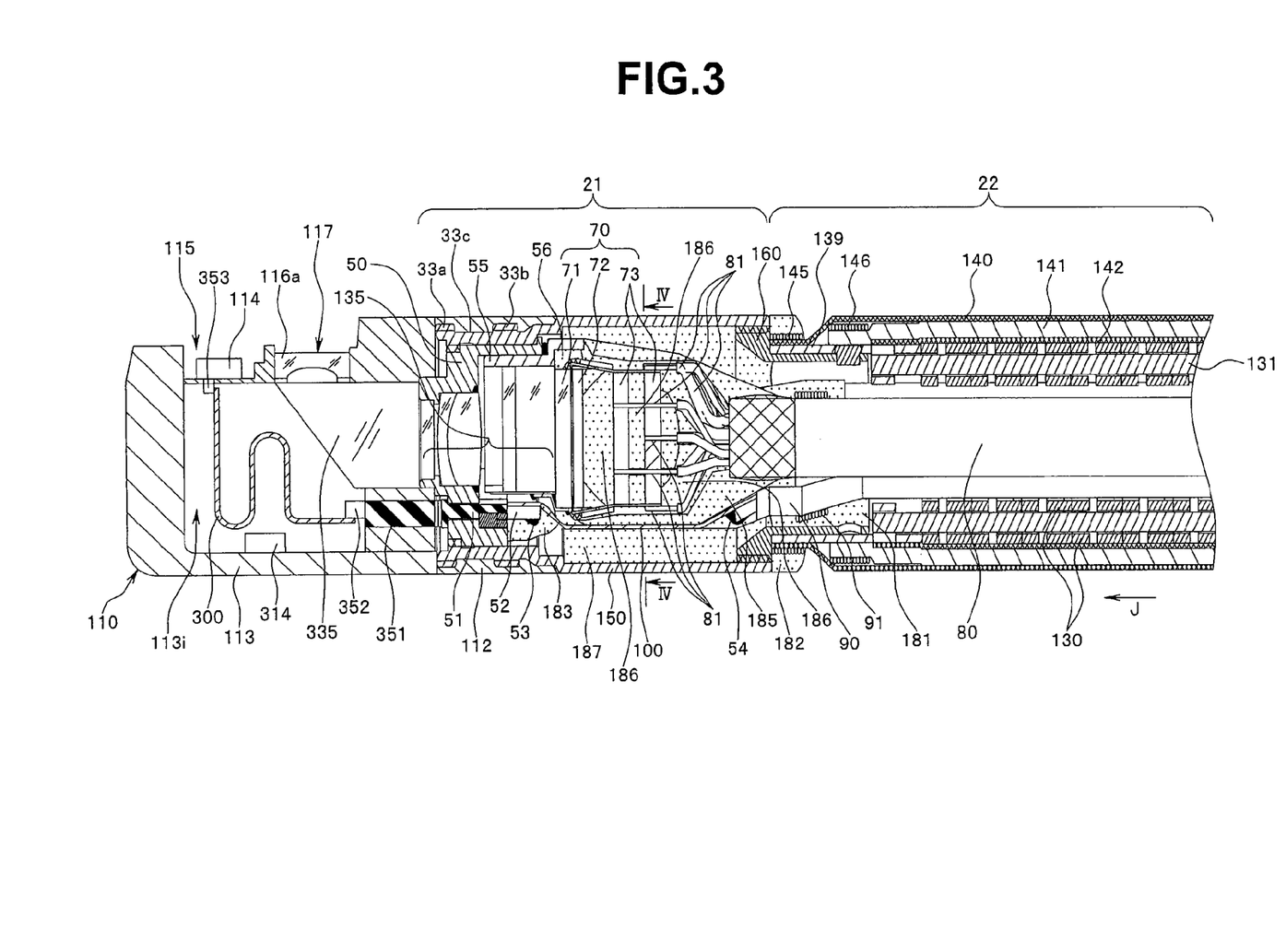
FIG. 3 is a partial sectional view taken along the line III-III in FIG. 2 and schematically showing a configuration of the adapter, the distal end portion, and a bending portion in the state where the adapter is attached to the distal end portion in FIG. 2.

Further, by changing the inclined angle of the bending operation lever 31, the operator makes the bending portion 22 bend in the inclined direction at an angle corresponding to the inclined angle of the bending operation lever 31 via the bending operation wire 131 (see FIG. 3). Note that in the operation portion 24, there are arranged various switches (not shown) for instructing various image pickup operations of an image pickup portion 70 (see FIG. 3), as will be described below, in addition to the bending operation lever 31.

The apparatus main body 3 which is connected to an end portion of the universal cord 26 extended from the operation portion 24 has, for example, a box shape. In the inside of the apparatus main body 3, which is covered by an exterior housing 35 formed by, for example, magnesium die casting, there are arranged a substrate (not shown) on which a plurality of electrical components, such as a CPU for image processing, are fixed, a battery unit (not shown) which supplies electric power to LEDs 114 (see FIG. 2) as will be described below, and the like.

Further, a monitor 7 which displays an endoscopic image picked up by the image pickup portion 70 (see FIG. 3) of the endoscope 2 is fixed to the exterior housing 35 of the apparatus main body 3 in an openable and closable manner with respect to the exterior housing 35. Note that the monitor 7 may be detachably attachable to and from the exterior housing 35.

In order to improve the portability of the apparatus main body 3, a belt 10 for hanging the apparatus main body 3 from a shoulder or the like of the operator is fixed to the exterior housing 35 at two points in a freely attachable and detachable manner to, for example, the apparatus main body 3.

Further, for example, four leg portions 58 for placing the apparatus main body 3, which are formed of rubber (for example NBR) or the like, are fixed to four sides of the box-shaped exterior housing 35.

Next, a configuration on the distal end side of the insertion portion 20 and a configuration of an adapter 10 will be described with reference to FIG. 2.

As shown in FIG. 2, the adapter 110 is mainly configured by including a detachable ring 112 and a hood portion 113. The hood portion 113 is a substantially cylindrical exterior member whose distal end portion is formed as a curved surface.

In the hood portion 113, there are provided the LEDs 114 which are electrical components and configure a light source for illuminating an examination object by supply of electric power, and a side view optical system 116 including a plurality of lenses. Note that in the hood portion 113, there may be provided a temperature sensor 314 (see FIG. 3) which is an electrical component for measuring the temperature in the adapter 110 by supply of electric power, and which will be described below.

On one side surface 113a side of the hood portion 113, there are formed an illumination hole 115 through which the LEDs 114 are faced, and an optical portion hole 117 in which an observation window 116a of the side view optical system 116 is arranged.

Over the whole outer circumfential surface at the distal end position of a cover member 150 configuring the outer circumfential surface of the distal end portion 21 of the insertion portion 20, a male screw portion 33a is projectingly provided in the radial direction of the distal end portion 21.

Further, at a position on the rear end side in the insertion direction J (hereinafter referred to simply as rear end side) from the male screw portion 33a in the distal end portion 21, a male screw portion 33b is projectingly provided in the radial direction of the distal end portion 21 over the whole circumference of the outer circumfential surface of the cover member 150.

The male screw portion 33a is formed to have a width narrower than that of the male screw portion 33b along the insertion direction J, and a sliding portion 33c is formed between the male screw portion 33a and the male screw portion 33b in the insertion direction.

The male screw portion 33a and the male screw portion 33b are configured to fix the adapter 110 to the distal end portion 21, by being screwed into a female screw portion (not shown) formed on the inner circumfential surface of the detachable ring 112 according to the rotation of the detachable ring 112 at the time when the adapter 110 is attached to the distal end portion 21 as shown in FIG. 3, as will be described below.

A rotation stopping portion 34, and electrical contacts 52 which are first contacts, are provided on the distal end surface 32a of the distal end portion 21 so as to project to the distal end side. The rotation stopping portion 34 is configured to position the adapter 110 attached to the distal end portion 21, and to protect the electrical contact 52.

Next, an internal configuration of the adapter 110, an internal configuration of the distal end portion 21, and an internal configuration of the distal end (hereinafter referred to simply as distal end) side in the insertion direction J of the bending portion 22 will be described with reference to FIG. 3 and FIG. 4.

FIG. 3 is a partial sectional view taken along the line III-III in FIG. 2 and schematically showing a configuration of the adapter, the distal end portion, and the bending portion in the state where the adapter is attached to the distal end portion in FIG. 2. FIG. 4 is a sectional view taken along the line IV-IV in FIG. 3 and schematically showing a configuration of the distal end portion.

As shown in FIG. 3, an objective optical system 135 and the image pickup portion 70 are provided in the distal end portion 21, specifically, in the inside covered by the tubular cover member 150 formed of a metal.

Note that the main part of the image pickup portion 70 is configured by an image pickup device 72 such as a CCD (hereinafter referred to as CCD), a cover glass 71, electrical substrates 73, a plurality of image pickup lines 81 for image pickup, and respective fillers 185 and 186.

Note that in the present embodiment, the position covered by the cover member 150 is defined as the distal end portion 21, and a portion which is on the rear side than the cover member 150 and on the distal end side than the flexible tube portion 23 is defined as the bending portion 22.

A plurality of lenses positioned on the distal end side of the objective optical system 135 are fitted and fixed to the inner circumference of an objective lens frame 50, so as to thereby be held by the objective lens frame 50. Further, a through hole penetrated along the insertion direction J is formed in the objective lens frame 50, and the electrical contact 52 whose outer circumference is covered by an insulating member 51 is inserted into the through hole.

When the adapter 110 is attached to the distal end portion 21, the electrical contact 52 is brought into electrical contact with an electrical contact 352 which is a second contact covered by an insulating member 351 in the hood portion 113 of the adapter 110.

The distal end side of the cover member 150 which is extended along the distal end portion 21 in the insertion direction J, is screwed and fixed to the outer circumference of the objective lens frame 50. Further, the distal end side outer circumference of an element frame 55 is fitted and fixed to the rear end side inner circumference of the objective lens frame 50. A plurality of lenses positioned on the rear end side of the objective optical system 135 are fitted in the inner circumference of the element frame 55 so that the plurality of lenses are held by the element frame 55.

Note that when the adapter 110 is attached to the distal end portion 21, the objective optical system 135 is held by the objective lens frame 50 and the element frame 55 in a position where the optical axis of the objective optical system 135 coincides with the optical axis of a prism 335 in the adapter 110.

The CCD 72 and the cover glass 71 stuck on to the distal end surface of the CCD 72 are fixed by an adhesive 56 to the inner circumference on the rear end side of the element frame 55.

The plurality of electric substrates 73 are arranged on the rear end side of the CCD 72, and the electric substrates 73 are electrically connected to the CCD 72. Further, the filler 186 formed of, for example, transparent resin is filled between the CCD 72 and the electric substrate 73 and between the respective electric substrates 73. Note that the resin forming the filler 186 is not limited to the transparent resin, but any resin may be used as the filler 186.

Portions exposed from insulating skin resin of the plurality of image pickup lines 81 provided in an image-pickup cable 80 are electrically connected to the electric substrates 73, for example, by solder.

Further, the filler 185 formed of, for example, transparent resin is also filled around the outer circumference of the electric substrate 73, the plurality of image pickup lines 81, and the distal end side of the image pickup cable 80. Note that the resin forming the filler 185 is not limited to the transparent resin, but any resin may be used as the filler 185.

The image pickup cable 80, the outer circumference of which is configured by braided metal element wires for noise preventing measures, is inserted into the insertion portion 20, the operation portion 24 and the universal cord 26, so that the plurality of image pickup lines 81 are electrically connected to the substrate in the apparatus main body 3, on which substrate the plurality of electrical components, such as the CPU for image processing, are fixed. The plurality of image pickup lines 81 are configured to perform transmission and reception of an image pickup signal between the image pickup portion 70 and the substrate in apparatus main body 3, on which substrate the plurality of electrical components, such as the CPU for image processing, are fixed.

Further, electrical components, such as a capacitor and an IC, are mounted on the electric substrate 73. Here, the industrial endoscope 2 includes a type in which the insertion portion 20 is as long as 10 meters. This may result in a case where an output signal received from the CCD 72 via the plurality of image pickup lines 81 in the image pickup cable 80 inserted in the insertion portion 20, and a drive signal to drive the CCD 72 via the plurality of image pickup lines 81, are liable not only to be attenuated, but to be distorted. The electric substrate 73 has a function to amplify the output signal and the drive signal which are attenuated and distorted due to the length of the image pickup cable 80.

Further, a power supply line for power supply 90 which supplies electric power to the LED 114, and which is covered by an insulating skin resin, is inserted in the insertion portion 20, the operation portion 24, and the universal cord 26.

The distal end of the power supply line 90 is positioned on the rear end side than the image pickup portion 70 in the space inside the cover member 150. The distal end portion of the power supply line 90, which portion is exposed by peeling the skin resin, is electrically connected, for example by solder 54, with the rear end of a flexible substrate (hereinafter referred to as FPC) 100 which is a thin plate first flexible substrate having a thickness of, for example, 0.5 mm.

That is, the rear end of the FPC 100 is electrically connected to the distal end of the power supply line 90 in the space inside the cover member 150. This is because when the connecting portion between the rear end of the FPC 100 and the distal end of the power supply line 90 is positioned in the space inside the bending portion 22, the above described connecting portion or the FPC 100 may be disconnected due to a bending load caused at the time when the bending portion 22 is bent.

Therefore, by positioning the above described connecting portion in the space inside the cover member 150 of the distal end portion 21 as shown in FIG. 3, it is possible to prevent the disconnection of the above described connecting portion or the FPC 100 due to the bending operation.

Figure 4:
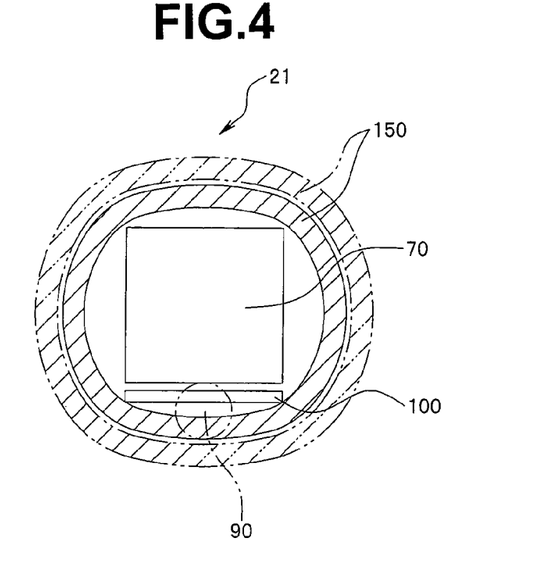
FIG. 4 is a sectional view taken along the line IV-IV in FIG. 3 and schematically showing a configuration of the distal end portion.

Further, the FPC 100 is inserted in a position between the outer circumference of the image pickup portion 70 and the inner circumference of the cover member 150 in the inside of the distal end portion 21, specifically, in a position close to the outer circumference of the image pickup portion 70, and more specifically, in a position in contact with the filler 185 which is filled in the lower portion of the image pickup portion 70, as shown in FIG. 3 and FIG. 4. Also, the distal end of FPC 100 is electrically connected to the electrical contact 52 by, for example, solder 53.

Thereby, when the adapter 110 is attached to the distal end portion 21, the electric power supplied from the battery unit provided in the apparatus main body 3, is supplied to the LED 114 via the power supply line 90, the FPC 100, the electrical contact 52, the electrical contact 352 of the LED 114 in the adapter 110, an FPC 300 one end of which is connected to the electrical contact 352, and which is a second flexible substrate provided in an inner portion 113i inside the hood portion 113, and an electrical contact 353 which is a third contact of the LED 114. That is, the FPC 100 connects the distal end of the power supply line 90 to the contact of the LED 114.

As shown in FIG. 3, the power supply line 90 is fixed, on the distal end side thereof, to the outer circumference of the image pickup cable 80 by a spool 91 which is a fixing member and is formed of Kevlar, or the like. Note that the spool 91 is wound, and thereafter the spool shape thereof is fixed by an adhesive 181.

This is because of the following reason. As will be described below, when the insertion portion 20 is formed, there is generally used a method in which after respective components are attached in the distal end portion 21, the bending portion 22 is assembled to the distal end portion 21, and the flexible tube portion 23 is assembled to the bending portion 22. However, if the power supply line 90 is not fixed at the time of the assembling of the bending portion 22 and the flexible tube portion 23, the connecting portion between the rear end of the FPC 100 and the distal end of the power supply line 90 or the FPC 100 may be disconnected when the power supply line 90 is pulled toward the rear end side.

Therefore, by fixing the distal end side of the power supply line 90 to the outer circumference of the image pickup cable 80 by the spool 91, it is possible to prevent the disconnection of the connecting portion between the rear end of the FPC 100 and the distal end of the power supply line 90 or the disconnection of the FPC 100 at the time of the assembling of the bending portion 22 and the flexible tube portion 23.

Further, by fixing the distal end side of the power supply line 90 to the outer circumference of the image pickup cable 80 by the spool 91, it is possible to prevent a filler 187, as will be described below, from being filled in the space inside the distal end portion 21, in the state where the connecting portion between the rear end of the FPC 100 and the distal end of the power supply line 90, and the cover member 150 are brought into contact with each other and short-circuited with each other.

Further, the filler 185 in contact with the FPC 100 covering the image pickup portion 70 is filled in the cover member 150, and the filler 187 formed of, for example, transparent resin is also filled in the space in the cover member 150.

Note that the resin forming the filler 187 is not limited to the transparent resin, but any resin may be used as the filler 187. Thereby, it is possible to prevent the filler 187, as will be described below, from being filled in the state where the connecting portion between the rear end of the FPC 100 and the power supply line 90, and the cover member 150 are brought into contact with each other and short-circuited with each other.

The distal end of a tubular connecting member 160 is fitted and fixed to the inner circumference at the rear end of the cover member 150. Further, a tubular bending portion distal end rigid portion 139 is fitted and fixed to the outer circumference of a portion of the connecting member 160, which portion is positioned in the bending portion 22.

The distal end of a plurality of bending pieces 130 provided in the bending portion 22 is arranged on the rear end side of the bending portion distal end rigid portion 139. Note that the distal end of the bending operation wire 131 inserted in the insertion portion 20 is fixed to the rear end of the bending portion distal end rigid portion 139. Further, the outer circumference of the bending pieces 130 is covered by an inner blade 142 along the insertion direction J.

The inner blade 142 prevents the bending portion 22 from being rotated in the circumferential direction at the time when the bending portion 22 is bent in a set direction by the towing and slackening of the bending operation wire 131, and prevents the breakage of a rubber tube 141, as will be described below, due to the bending.

The distal end side of the rubber tube 141 covering the outer circumference of the inner blade 142 is fixed to the outer circumference on the rear end side of the bending portion distal end rigid portion 139 by a spool 146 formed of Kevlar or the like. The rubber tube 141 is provided to ensure the water tightness of the bending portion 22.

Further, an outer blade 140 is covered on the outer circumference of the rubber tube 141. The distal end of the outer blade 140 is fixed by a spool 145 formed of Kevlar or the like, on the distal end side than the position where the distal end of the rubber tube 141 is fixed to the bending portion distal end rigid portion 139. Note that the spool shape of the wound spool 145 is fixed by an adhesive 182.

The outer blade 140 is formed by a net tube of metal element wires, and thereby prevents, when the insertion portion 20 is inserted into, for example, the inside of a jet engine, the bending portion 22 from being damaged due to the contact with a component, or the like, inside the jet engine.

Next, there will be briefly described a method for assembling the distal end portion 21 configured as described above.

First, the plurality of electric substrates 73 are electrically connected to the rear end side of the CCD 72. Then, the distal end of the plurality of image pickup lines 81 of the image pickup cable 80, which distal end is exposed from insulating skin resin, is electrically connected to the electric substrate 73.

Then, the filler 186 is filled between the CCD 72 and the electric substrates 73, and between the respective electric substrates 73. Also, the filler 185 is applied to the outer circumference of the electric substrates 73, the plurality of image pickup lines 81, and the distal end side of the image pickup cable 80.

Subsequently, after the fillers 186 and 185 are hardened, the CCD 72 and the cover glass 71 are fixed, by using the adhesive 56, to the inner circumference on the rear end side of the element frame 55 in which some of the lenses of the objective optical system 135 is fixed. As a result, the image pickup portion 70 is formed.

Then, the outer circumference of the distal end side of the element frame 55 is fitted and fixed to the inner circumference on the rear end side of the objective lens frame 50 which holds the lens positioned on the distal end side of the objective optical system 135.

Then, the electrical contact 52 whose outer circumference is covered with the insulating member 51 is inserted and fixed in the through hole of the first objective lens frame 50, and thereafter the distal end of the FPC 100 is electrically connected to the electrical contact 52 with the solder 53.

Then, as shown in FIG. 3 and FIG. 4, the FPC 100 is inserted in the lower vicinity of the outer circumference of the image pickup portion 70, and thereafter the distal end of the exposed power supply line 90 is electrically connected to the rear end of the FPC 100 with the solder 54. Thereafter, the power supply line 90 is fixed to the outer circumference of the image pickup cable 80 by the spool 91, and then the wound spool 91 is fixed with the adhesive 181.

Finally, the distal end side of the cover member 150 is fixed, by the screw, to the outer circumference of the objective lens frame 50, and the outer circumference of the distal end portion 21 is covered by the cover member 150 so that at least the connecting portion between the rear end of the FPC 100 and the distal end of the power supply line 90 is covered by the cover member 150. Then, the filler 187 is filled in the space between the outer circumference of the image pickup portion 70 and the cover member 150. Thereby, the distal end portion 21 is formed.

As described above, in the present embodiment, it is described that the FPC 100 is inserted in a position near the outer circumference of the image pickup portion 70 in the distal end portion 21, and that the distal end of the FPC 100 is electrically connected to the electrical contact 52, and the rear end of the FPC 100 is electrically connected to the distal end of the power supply line 90.

Thereby, as compared with the conventional configuration in which the power supply line 90 shown by the two-dot chain line in FIG. 4 is inserted in the position near the outer circumference of the image pickup portion 70, and in which the distal end of the power supply line 90 is electrically connected to the electrical contact 52, it is possible in the present embodiment to make the cover member 150 thinner, as shown by the cross sections represented by the solid lines and the two-dot chain lines in FIG. 4, because as shown in FIG. 4, the FPC 100 having a smaller occupation area than that of the power supply line in the distal end portion 21 in a plan view is inserted near the outer circumference of the image pickup portion 70. That is, the diameter near the outer circumference of the image pickup portion 70 in the distal end portion 21 can be reduced as compared with conventional one.

Thereby, it is possible to provide the endoscope 2 having a configuration which is capable of realizing the reduction in the diameter of the distal end portion 21.

Note that in the present embodiment, the adapter 110 is described by taking as an example the side view type adapter having the side view optical system 116, but the present invention is not limited to this. It is needless to say that the same effect as that of the present embodiment can be obtained when a direct view type adapter having a direct view optical system is used.

Further, in the present embodiment, it is described that the electric power is supplied to the LED 114 in the adapter 110 via the power supply line 90, the FPC 100, the electrical contacts 52 and 352, the FPC 300, and the electrical contact 353, but the present invention is not limited to this. The electric power may be supplied to the temperature sensor 314 in the adapter 110 via the power supply line 90, the FPC 100, the electrical contacts 52 and 352, the FPC 300, and the electrical contact 353.

Further, in the present embodiment, it is described that the electric power is supplied to the LED 114 in the adapter 110 via the power supply line 90, the FPC 100, the electrical contacts 52 and 352, the FPC 300, and the electrical contact 353, but the present invention is not limited to this. It may be configured such that the distal end of the FPC 100 is electrically connected directly to the electrical contact 353 of the LED 114 in the case of an endoscope in which the adapter 110 is not the attachable and detachable type and is fixed to the distal end portion 21.

Further, in the present embodiment, as shown in FIG. 2 and FIG. 3, it is described that the adapter 110 is detachably attached to the distal end of the distal end portion 21, but the present invention is not limited to this. The present embodiment may be applied to a direct view type endoscope in which the adapter 110 is not used.

Figure 5:
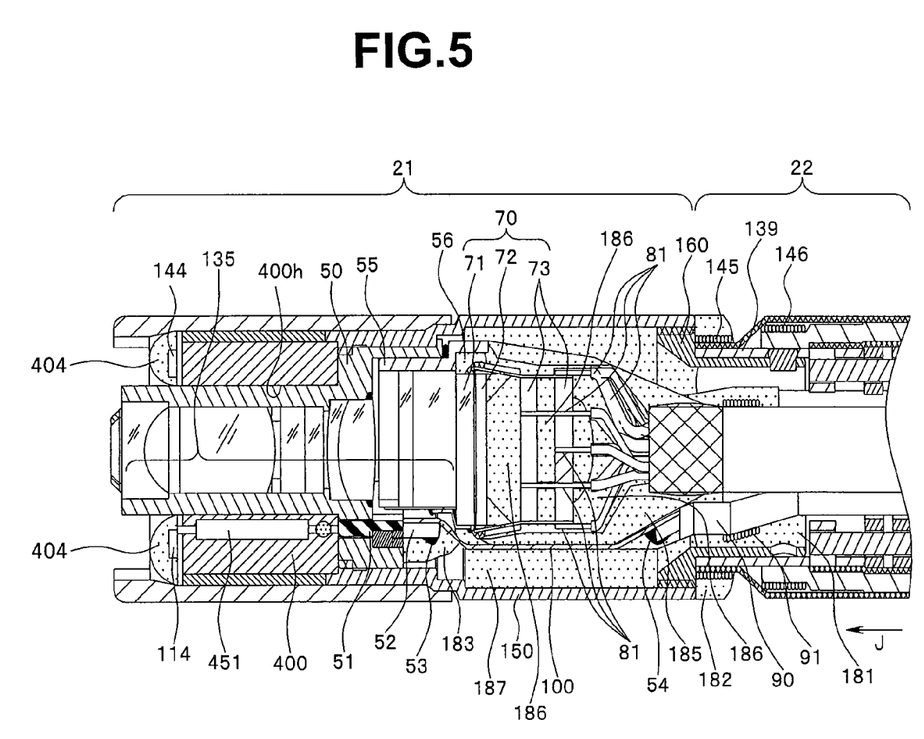
FIG. 5 is a partial sectional view schematically showing a configuration of the distal end portion and the bending portion of the insertion portion of a direct view type endoscope in which the adapter is not used.

In the following, an example in which the present embodiment is applied to the direct view type endoscope without the adapter 110, will be described with reference to FIG. 5. FIG. 5 is a partial sectional view schematically showing a configuration of the distal end portion and the bending portion of the insertion portion of a direct view type endoscope in which the adapter is not used.

As shown in FIG. 5, a distal end rigid portion 400 is provided inside the distal end portion 21 of the direct view type endoscope in which the adapter is not used. A through hole 400$h$ along the insertion direction J is formed at the approximate center of the distal end rigid portion 400.

The objective lens frame 50 is inserted in the through hole 400$h$, and a distal end side lens group of the objective optical system 135 is held by the objective lens frame 50.

Further, the plurality of LEDs 114 as described above are provided so as to surround, for example, the distal end side lenses of the objective optical system 135 in the plan view of the lenses, and each of the LEDs 114 is sealed by, for example, hemispherical LED sealing resin 404.

Further, a terminal 451 is inserted in the distal end rigid portion 400 along the insertion direction J. One end of the terminal 451 is electrically connected to the LED 114, and the other end of the terminal 451 is electrically connected to the electrical contact 52. Note that the other configuration is the same as that of the present embodiment as shown in FIG. 1 to FIG. 4.

According to such configuration, the electric power supplied from the battery unit provided in the apparatus main body 3 is supplied to the LED 114 via the power supply line 90, the FPC 100, the electrical contact 52, and the terminal 451.

Even in such configuration, it is possible to obtain the same effect as that of the above described present embodiment, because the FPC 100 which electrically connects the distal end of the power supply line 90 to the electrical contact 52, is inserted in the position between the outer circumference of the image pickup unit 70 and the inner circumference of the cover member 150.

That is, it is possible to provide the endoscope having the configuration which is capable of realizing the reduction in the diameter of the distal end portion 21.

Note that the same effect can be obtained even when the above described configuration is applied to a side view type endoscope in which the adapter 110 is not used.

Further, it is described that in FIG. 5, the electric power is supplied to the LED 114 of the distal end portion 21 via the power supply line 90, the FPC 100, the electrical contact 52, and the terminal 451, but the present invention is not limited to this. The electric power may be supplied to the temperature sensor (not shown) via the power supply line 90, the FPC 100, the electrical contact 52, and the terminal 451.

Second Embodiment

Figure 6:
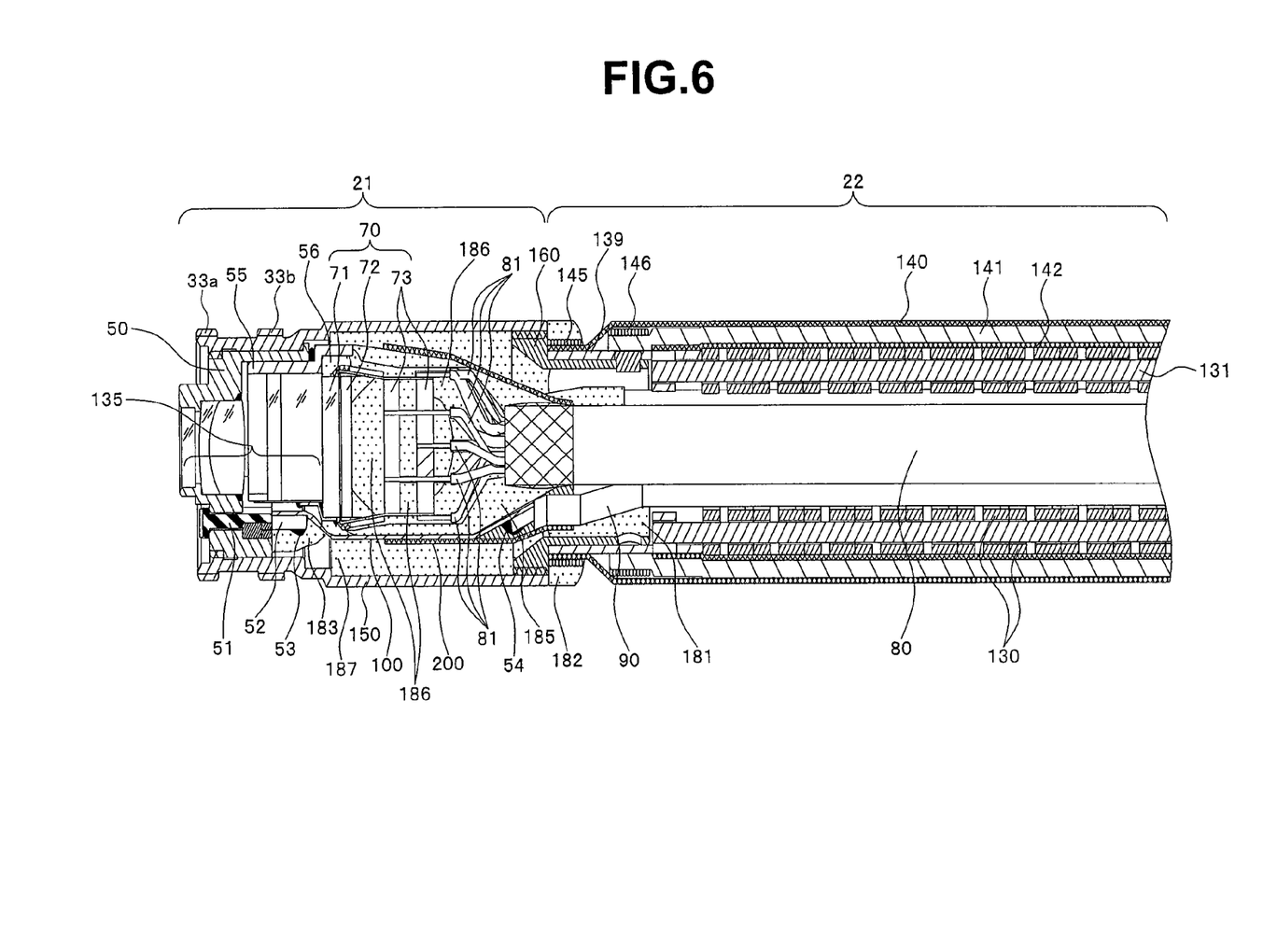
FIG. 6 is a partial sectional view schematically showing a configuration of the distal end portion and the bending portion of the insertion portion of an endoscope according to a second embodiment.

FIG. 6 is a partial sectional view schematically showing a configuration of the distal end portion and a bending portion of an insertion portion of an endoscope according to the present embodiment.

The configuration of the endoscope according to the second embodiment is different from the endoscope shown in FIG. 1 to FIG. 4 in the method for fixing the power supply line to the image pickup cable. Therefore, only the difference will be described. The same components as those in the first embodiment are denoted by the same reference numerals and characters, and explanation thereof is omitted.

As shown in FIG. 6, both of the rear half portion of the FPC 100 in the insertion direction J (hereinafter referred to simply as the rear half portion) and the distal end side of the power supply line 90 are covered by a heat shrinkable tube 200 which is a fixing member and formed of an insulating member, so as to thereby be fixed to the outer circumference of the image pickup portion 70, specifically, to the outer circumference of the hardened filler 185 and the outer circumference of the image pickup cable 80. As a result, the FPC 100 is fixed integrally with the image pickup portion 70.

Note that the heat shrinkable tube 200 is made to cover the rear half portion of the FPC 100 and the distal end side of the power supply line 90, and thereafter is applied with heat with, for example, a heat gun, so as to shrink and thereby fix the rear half portion of the FPC 100 and the distal end side of the power supply line 90 to the outer circumference of the image pickup portion 70 and the outer circumference of the image pickup cable 80.

In this way, even in the case where the heat shrinkable tube 200 is used, it is possible to prevent the disconnection of the connecting portion between the rear end of the FPC 100 and the distal end of the power supply line 90, or the disconnection of the FPC 100 at the time when the bending portion 22 and the flexible tube portion 23 are assembled to the distal end portion 21, in the same way as in the configuration in which the distal end side of the power supply line 90 is fixed to the outer circumference of the image pickup cable 80, by the spool 91 as shown in the above described first embodiment.

Further, it is possible to prevent the filler 187 from being filled in the state where the connecting portion between the rear end of the FPC 100 and the distal end of the power supply line 90, and the cover member 150 are brought into contact with each other and short-circuited with each other before the filler 187 is filled.

Further, the fixation by the spool as in the above described first embodiment need not be performed, and the fixation of the FPC 100 and the power supply line 90 can be effected only by applying heat to the heat shrinkable tube 200 with the heat gun. Thereby, the workability can be improved as compared with the first embodiment.

Further, the heat shrinkable tube 200 is formed of an insulating member, and covers the connecting portion between the rear end of the FPC 100 and the distal end of the power supply line 90. Thus, it is possible to more surely prevent the filler 187 from being filled in the state where the connecting portion and the cover member 150 are brought into contact with each other and short-circuited with each other, as compared with the above described first embodiment. Note that the other effects are the same as those of the above described first embodiment.

Figure 7:
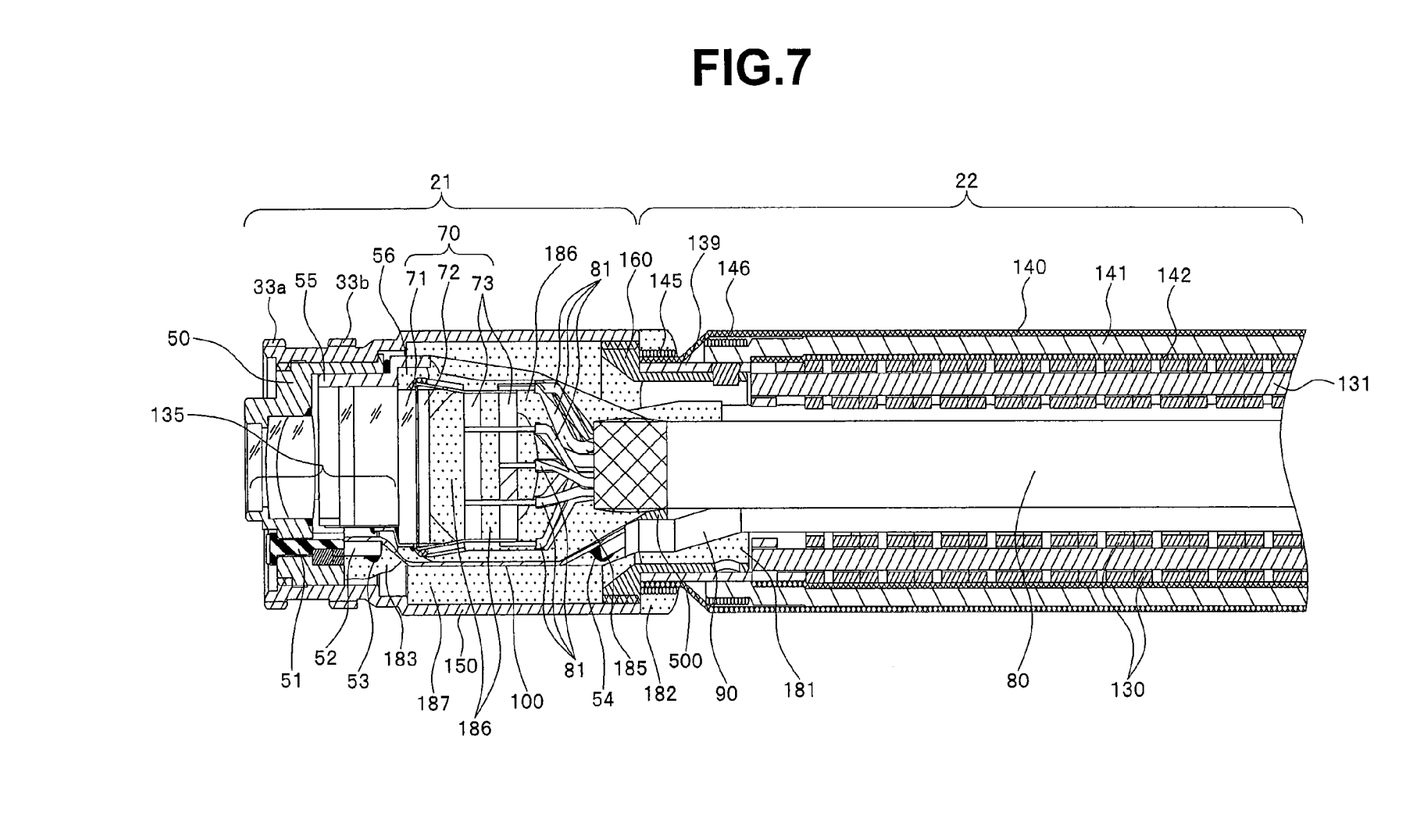
FIG. 7 is a partial sectional view schematically showing a modification example of the distal end portion and the bending portion of the insertion portion of the endoscope shown in FIG. 6.

In the following, a modification example will be described with reference to FIG. 7. FIG. 7 is a partial sectional view schematically showing a modification example of the distal end portion and the bending portion of the insertion portion of the endoscope shown in FIG. 6.

In the present embodiment, it is described that the rear half portion of the FPC 100 and the distal end side of the power supply line 90 are fixed by the heat shrinkable tube 200 to the outer circumference of the image pickup portion 70 and the outer circumference of the image pickup cable 80.

The present invention is not limited to this. The rear half portion of the FPC 100 and the distal end side of the power supply line 90 may be fixed to the outer circumference of the image pickup portion 70 and the outer circumference of the image pickup cable 80, for example, by an epoxy based adhesive 500 which serves as the fixing member and has high temperature heat resistance, instead of the heat shrinkable tube 200.

Even by such configuration, it is not only possible to obtain the same effects as those in the above described first embodiment, but also possible to make the inside diameter of the distal end portion 21 around the image pickup portion 70 smaller by the thickness of the heat shrinkable tube 200, as compared with the present embodiment, because of the configuration in which the heat shrinkable tube 200 is not used.

Note that the present embodiment may be applied to a configuration in which the direct view type adapter or the side view type adapter is detachably attached to the distal end portion, and may also be applied to the direct view type or the side view type endoscope in which the adapter is not used. Further, the present embodiment is not limited to the configuration in which the electric power is supplied to the LED 114, but may be applied to a configuration in which the electric power is supplied to the temperature sensor 314.

Third Embodiment

Figure 8:
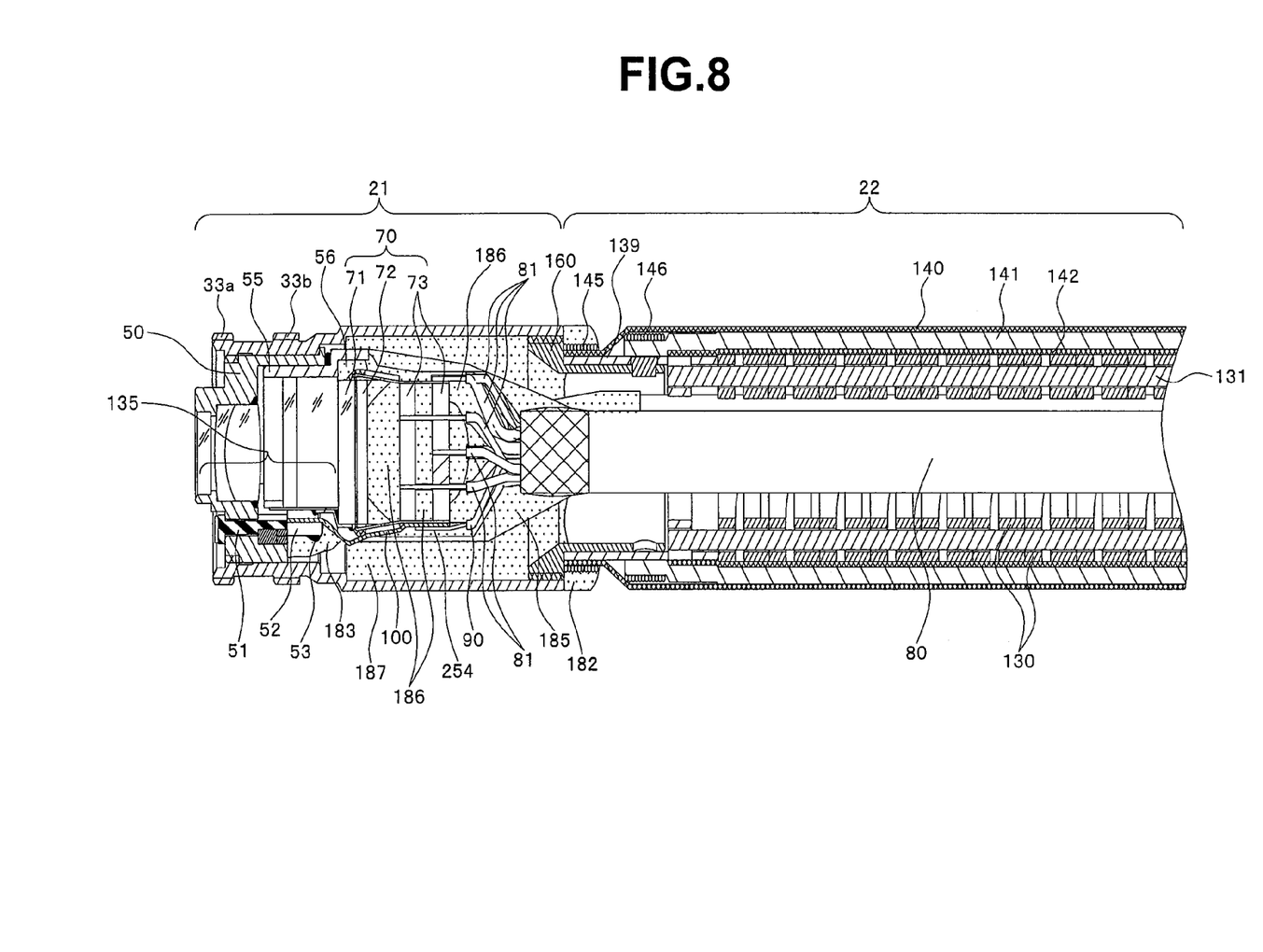
FIG. 8 is a partial sectional view schematically showing a configuration of the distal end portion and the bending portion of the insertion portion of an endoscope according to a third embodiment.

FIG. 8 is a partial sectional view schematically showing a configuration of the distal end portion and a bending portion of an insertion portion of an endoscope according to the present embodiment.

The configuration of the endoscope according to the third embodiment is different from the above described endoscope shown in FIG. 1 to FIG. 4 in the connection method between the FPC and the power supply line. Therefore, only the difference will be described. The same components as those in the first embodiment are denoted by the same reference numerals and characters, and explanation thereof is omitted.

As shown in FIG. 8, in the present embodiment, the rear end of the FPC 100 is electrically connected to positions of the plurality of electric substrates 73, which positions are exposed from the filler 185.

Further, the power supply line 90 is inserted in the image pickup cable 80 together with the image pickup line 81. Specifically, the power supply line 90 and the image pickup line 81 are braided together with metal element wires which are braided around the outer circumference of the image pickup cable 80.

Further, the distal end of the power supply line 90 is electrically connected to the plurality of electric substrates 73, for example, by solder 254. As a result, the distal end of the power supply line 90 and the rear end of the FPC 100 are electrically connected to each other via the electric substrate 73.

According to such configuration, it is possible to prevent the disconnection of the connecting portion between the rear end of the FPC 100 and the distal end of the power supply line 90 or the FPC 100 at the time when the bending portion 22 and the flexible tube portion 23 are assembled to the distal end portion 21. It is also possible to more surely prevent the filler 187 from being filled in the state where the connecting portion between the rear end of the FPC 100 and the distal end of the power supply line 90, and the cover member 150 are brought into contact with each other and short circuited with each other before the filler 187 is filled, as compared with the first embodiment.

Further, when the bending portion 22 and the flexible tube 23 are assembled to the distal end portion 21, both of the image pickup cable 80 and the power supply line 90 need to be considered in the first embodiment and the second embodiment, as described above. However, in the present embodiment, only the image pickup cable 80 is considered and assembled, so that the workability is improved.

Further, the FPC 100 is electrically connected directly to the electric substrate 73, so that the diameter of the circumference of the image pickup portion 70 of the distal end portion 21 can be made smaller as compared with the above described first embodiment. Further, the heat shrinkable tube 200 and the epoxy based adhesive 500 need not be used as in the second embodiment. Thus, it is not only possible to make the diameter of the circumference of the image pickup portion 70 of the distal end portion 21 smaller as compared with the above described second embodiment, but also possible to reduce the manufacturing cost.

Further, the present embodiment may also be applied to a configuration in which the direct view type or the side view type adapter is detachably attached to the distal end portion 21, and may also be applied to the direct view type or the side view type endoscope in which the adapter is not used. Further, the present embodiment is not limited to the configuration in which the electric power is supplied to the LED 114, but the present embodiment may be applied to a configuration in which the electric power is applied to the temperature sensor 314.

Further, in the above described first to third embodiments, the endoscope is explained by taking as an example one included in a shoulder type industrial endoscope apparatus which is excellent in portability, but the present invention is not limited to this. The present invention may of course be applied to an endoscope included in a large-sized industrial endoscope apparatus in which the insertion portion is housed in the apparatus main body.

The present invention described in the above embodiments is not limited to the above described embodiments, and various modifications are possible in an implementation stage within the scope and spirit of the present invention. Further, various stages of the present invention are included in the above described embodiments, and various inventions may be extracted by properly combining the plurality of disclosed constitution elements.

For example, even when several constitution elements are eliminated from all the constitution elements as shown in the embodiment, it is possible to solve the above described problem. When an effect as described as the effect of the present invention is obtained, the configuration in which the constitution elements are eliminated may also be extracted as the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
   an elongated insertion portion inserted in an examination object;
   an electrical component which is provided in a distal end portion on a distal end side in an insertion direction of the insertion portion and is driven by supply of electric power;
   a rectangular-shaped image pickup portion which is provided in an inside of the distal end portion covered by a tubular cover member configuring an outer circumference of the distal end portion, so as to be located on a rear end side in the insertion direction than the electrical component, and which picks up an image of the examination object;
   a power supply line for power supply, a distal end in the insertion direction of which is positioned on the rear end side in the insertion direction than the image pickup portion in the inside of the distal end portion covered by the cover member, the power supply line being inserted in the insertion portion; and
   a thin plate-like flexible substrate which extends along the insertion direction in a space, the space being circumscribed by an outer circumferential surface of the image pickup portion in the distal end portion and an inner circumferential surface of the distal end portion, the thin plate-like flexible substrate electrically connecting a contact of the electrical component to the distal end of the power supply line,
   wherein the flexible substrate is supported on one side thereof by a fixing member formed of an insulating material and on an opposed side thereof by a filler material.

2. The endoscope according to claim 1,
   wherein the flexible substrate is inserted in a position close to the outer circumference of the image pickup portion in the distal end portion.

3. The endoscope according to claim 1,
   wherein the electrical component is a light source which illuminates the examination object by supply of electric power via the power supply line, the flexible substrate, and the contact.

4. The endoscope according to claim 1,
   wherein the electrical component is a temperature sensor which measures the temperature in the distal end portion by supply of electric power via the power supply line, the flexible substrate, and the contact.

5. The endoscope according to claim 1,
wherein an electric substrate which amplifies a drive signal for operating the image pickup portion and an output signal from the image pickup portion, is electrically connected to the rear end in the insertion direction of the image pickup portion, and an image pickup line for image pickup which is included in an image pickup cable for transmitting the drive signal and the output signal between the image pickup portion and an external device, is electrically connected to the electric substrate, and
wherein the power supply line is fixed to an outer circumference of the image pickup cable by a fixing member.

6. The endoscope according to claim 5,
wherein the fixing member is a heat shrinkable tube.

7. The endoscope according to claim 1,
wherein in the distal end portion, the flexible substrate and the power supply line are fixed to the outer circumference of the image pickup portion and the outer circumference of the image pickup cable integrally with the image pickup portion by a fixing member.

8. The endoscope according to claim 1,
wherein an electric substrate which amplifies a drive signal for operating the image pickup portion and an output signal from the image pickup portion is electrically connected to the rear end in the insertion direction of the image pickup portion, and an image pickup line for image pickup which is included in an image pickup cable for transmitting the drive signal and the output signal between the image pickup portion and an external device, is electrically connected to the electric substrate, and
wherein the flexible substrate is electrically connected to the electric substrate.

9. The endoscope according to claim 8,
wherein the power supply line is provided in the image pickup cable together with image pickup line.

10. The endoscope according to claim 1, wherein the thin plate-like flexible substrate extends along the insertion direction from a rear end of the image pickup portion and circumvents the image pickup portion.

11. The endoscope according to claim 1, wherein a position of the contact of the electrical component electrically connected to the flexible substrate and a position of the distal end of the power supply line are located on an inner side in a diameter direction of the distal end portion than a maximum external diameter portion of the image pickup portion, and
electric power is supplied to the electrical component via the power supply line, the flexible substrate, and the contact.

12. The endoscope according to claim 1, wherein the fixing member is a shrinkable tube.

13. An endoscope comprising:
an elongated insertion portion inserted in an examination object;
an electrical component which is provided in an adapter attached to a distal end portion on a distal end side in an insertion direction of the insertion portion, and is driven by supply of electric power;
a rectangular-shaped image pickup portion which is provided in an inside of the distal end portion covered by a tubular cover member configuring an outer circumference of the distal end portion, and which picks up an image of the examination object;
a power supply line for power supply, a distal end in the insertion direction of which is positioned on a rear end side in the insertion direction than the image pickup portion in the inside of the distal end portion covered by the cover member, the power supply line being inserted in the insertion portion; and
a thin plate-like flexible substrate which extends along the insertion direction in a space, the space being circumscribed by an outer circumferential surface of the image pickup portion in the distal end portion and an inner circumferential surface of the distal end portion, the thin plate-like flexible substrate electrically connecting a contact of the electrical component in the adapter to the distal end of the power supply line,
wherein the flexible substrate is supported on one side thereof by a fixing member formed of an insulating material and on an opposed side thereof by a filler material.

14. The endoscope according to claim 13,
wherein the flexible substrate is inserted in a position close to the outer circumference of the image pickup portion in the distal end portion.

15. The endoscope according to claim 13,
wherein the electrical component is a light source which illuminates the examination object by supply of electric power via the power supply line, the flexible substrate, and the contact.

16. The endoscope according to claim 13,
wherein the electrical component is a temperature sensor which measures the temperature in the distal end portion by supply of electric power via the power supply line, the flexible substrate, and the contact.

17. The endoscope according to claim 13,
wherein an electric substrate which amplifies a drive signal for operating the image pickup portion and an output signal from the image pickup portion, is electrically connected to the rear end in the insertion direction of the image pickup portion, and an image pickup line for image pickup which is included in an image pickup cable for transmitting the drive signal and the output signal between the image pickup portion and an external device, is electrically connected to the electric substrate, and
wherein the power supply line is fixed to an outer circumference of the image pickup cable by a fixing member.

18. The endoscope according to claim 17,
wherein the fixing member is a heat shrinkable tube.

19. The endoscope according to claim 13,
wherein in the distal end portion, the flexible substrate and the power supply line are fixed to the outer circumference of the image pickup portion and the outer circumference of the image pickup cable integrally with the image pickup portion by a fixing member.

20. The endoscope according to claim 13,
wherein an electric substrate which amplifies a drive signal for operating the image pickup portion and an output signal from the image pickup portion is electrically connected to the rear end in the insertion direction of the image pickup portion, and an image pickup line for image pickup which is included in an image pickup cable for transmitting the drive signal and the output signal between the image pickup portion and an external device, is electrically connected to the electric substrate, and
wherein the flexible substrate is electrically connected to the electric substrate.

21. The endoscope according to claim 20,
wherein the power supply line is provided in the image pickup cable together with image pickup line.

22. The endoscope of claim 13, wherein the thin plate-like flexible substrate extends along the insertion direction from a rear end of the image pickup portion and circumvents the image pickup portion.

23. The endoscope according to claim 13, wherein a position of the contact of the electrical component electrically connected to the flexible substrate and a position of the distal end of the power supply line are located on an inner side in a diameter direction of the distal end portion than a maximum external diameter portion of the image pickup portion, and electric power is supplied to the electrical component via the power supply line, the flexible substrate, and the contact.

24. The endoscope according to claim 13, wherein the fixing member is a shrinkable tube.

25. An endoscope comprising:

an elongated insertion portion inserted in an examination object;

an electrical component which is provided in an adapter detachably attached to a distal end portion on a distal end side in the insertion direction of the insertion portion, and is driven by supply of electric power;

a rectangular-shaped image pickup portion which is provided in an inside of the distal end portion covered by a tubular cover member configuring an outer circumference of the distal end portion, and which picks up an image of the examination object;

a power supply line for power supply, a distal end in the insertion direction of which is positioned on a rear end side in the insertion direction than the image pickup portion in the inside of the distal end portion covered by the cover member, the power supply line being inserted in the insertion portion;

a first thin plate-like flexible substrate which extends along the insertion direction in a space, the space being circumscribed by an outer circumferential surface of the image pickup portion in the distal end portion and an inner circumferential surface of the distal end portion, the first thin plate-like flexible substrate electrically connecting a first contact of the electrical component to the distal end of the power supply line, wherein the flexible substrate is supported on one side thereof by a fixing member formed of an insulating material and on an opposed side thereof by a filler material; and a second thin plate-like flexible substrate which, when the adapter is attached to the distal end portion, electrically connects, in the adapter, a second contact of the electrical component connected to the first contact, to a third contact of the electrical component.

26. The endoscope according to claim 25, wherein the first flexible substrate is inserted in a position close to an outer circumference of the image pickup portion in the distal end portion.

27. The endoscope of claim 25, wherein the first thin plate-like flexible substrate extends along the insertion direction from a rear end of the image pickup portion and circumvents the image pickup portion.

28. The endoscope according to claim 25, wherein a position of the contact of the electrical component electrically connected to the flexible substrate and a position of the distal end of the power supply line electrically connected to the flexible substrate are located on an inner side in a diameter direction of the distal end portion than a maximum external diameter portion of the image pickup portion, and electric power is supplied to the electrical component via the power supply line, the flexible substrate, and the contact.

29. The endoscope according to claim 25, wherein the fixing member is a shrinkable tube.

* * * * *